(12) United States Patent
Adachi et al.

(10) Patent No.: US 6,562,624 B2
(45) Date of Patent: May 13, 2003

(54) METHODS AND MATERIALS FOR THE RAPID AND HIGH VOLUME PRODUCTION OF A GENE KNOCK-OUT LIBRARY IN AN ORGANISM

(75) Inventors: Kiichi Adachi, Durham, NC (US); John E. Hamer, Durham, NC (US); Lisbeth Hamer, Durham, NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 0 days.

(21) Appl. No.: 09/826,630

(22) Filed: Apr. 5, 2001

(65) Prior Publication Data

US 2002/0061593 A1 May 23, 2002

Related U.S. Application Data

(63) Continuation-in-part of application No. 09/728,194, filed on Nov. 30, 2000, which is a continuation of application No. 09/270,620, filed on Mar. 17, 1999.

(51) Int. Cl.$^7$ .................................................. C12N 15/87
(52) U.S. Cl. .................................................... 435/463
(58) Field of Search ............................................ 435/463

(56) References Cited

U.S. PATENT DOCUMENTS

| 5,677,170 A | 10/1997 | Devine et al. |
| 5,728,551 A | 3/1998 | Devine et al. |
| 6,207,384 B1 * | 3/2001 | Mekalanos et al. ............ 435/6 |

FOREIGN PATENT DOCUMENTS

| WO | 9729202 | 8/1997 |
| WO | 9810077 | 3/1998 |
| WO | 9837205 | 8/1998 |
| WO | 9840510 | 9/1998 |

OTHER PUBLICATIONS

Migheli et al. Transposition of the autonomous Fot 1 element in the filamentous fungus *Fusarium oxysporum* Genetics vol. 151: 1005–1013, Mar. 9, 1999.*
Wang et al. pDUAL: a transposon–based cosmid cloning vector for genereating nested deletions and DNA sequencing templates in vivo. PNAS vol. 90:7874–7878, 1993.*
Sauer, B., "Multiplex Cre/lox recombination permits selective site–specific DNA targeting to both a natural and an engineered site in the yeast genome", Nucleic Acids Res1996 Dec 1:24(23):4608–13 Abstract Only.
Seibler, J. et al., "Double–reciprocal crossover mediated by FLP–recombinase: a concept and an assay", Biochemistry Feb. 1997 18;36(7):1740–7 Abstract Only.
Strathmann, M. et al., "Transposon–facilitated DNA sequencing", Proc Natl Acad Sci U S A Feb. 1991 15:88(4):1247–50 Abstract Only.
Phadnis, SH et at., "Tn5supF, a 264–base–pair transposon derived from Tn5 for insertion mutagenesis and sequencing DNAs cloned in phage lambda", Proc Natl Acad Sci U S A 1989 Aug;86(15):5908–12 Abstract Only.
Way, JC et al., "New Tn10 derivatives for transposon mutagenesis and for construction of IacZ operon fusions by transposition", Gene 1984 Dec;32(3):369–79 Abstract only.
Lee, SY et al., "Efficient Tn10 transposition into a DNA insertion hot spot in vivo requires the 5–methyl groups of symmetrically disposed thymines within the hot–spot consensus sequence", Proc Natl Acad Sci USA Nov. 1987; 84 (22): 7876–80 Abstract only.
Brown, PO et al., "Correct integration of retroviral DNA in vitro", Cell May 1987 8:49(3):347–56 Abstract only.
Eichinger, DJ et al., "The DNA intermediate in yeast Ty1 element transposition copurifies with virus–like particles: cell—free Ty1 transposition", Cell Sep. 1988 23:54(7):955–66 Abstract only.
Eichinger, DJ et al., "A specific terminal structure is required for Ty1 transposition", Genes Dev 1990 Mar;4(3):324–30 Abstract only.
Migheli, Q. et al., "Transposition of the autonomous Fot1 element in the filamentous fungus *Fusarium oxysporum*", Genetics 1999 Mar;151(3):1005–13 Abstract only.
Kleckner, N. et al., "Uses of Transposons with Emphasis on Tn10", Methods in Enzymology 1991; 204:139–180.

* cited by examiner

Primary Examiner—James Ketter
Assistant Examiner—William Sandals
(74) Attorney, Agent, or Firm—Laura L. Kiefer; Timothy G. Hofmeyer; Deborah H. Spencer (57) ABSTRACT

The present invention relates to methods for facilitating site directed homologous recombination in a eukaryotic organism to produce genomic mutants using transposon mediated mutagenesis of cosmid vectors carrying large genomic inserts from the target eukaryotic organism. The transposon carries a bifunctional marker that can be used for selection in both bacteria and the target eukaryotic organism. Minimization of the length of the cosmid vector allows for maximization of the size of the genomic insert carried by the cosmid. Maximization of the size of the genomic insert increases the frequency of homologous recombination with the genome of the target eukaryotic organism.

4 Claims, 4 Drawing Sheets

SEQUENCE LISTING

<160> NUMBER OF SEQ ID NOS: 9

<210> SEQ ID NO 1
<211> LENGTH: 12
<212> TYPE: DNA
<213> ORGANISM: bacteriophage lambda

<400> SEQUENCE: 1
gggcggcgac ct                                                    12

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tcgctcttga agggaactat g                                          21

<210> SEQ ID NO 3
<211> LENGTH: 17
<212> TYPE: DNA
<213> ORGANISM: Artificial Sequence
<220> FEATURE:
<223> OTHER INFORMATION: primer

<400> SEQUENCE: 3
ggcgttgtga tctgcag                                              17

<210> SEQ ID NO 4
<211> LENGTH: 17
<212> TYPE: DNA
<213> ORGANISM: Artificial Sequence
<220> FEATURE:
<223> OTHER INFORMATION: primer

<400> SEQUENCE: 4
ggccaggaaa ctcccag                                              17

<210> SEQ ID NO 5
<211> LENGTH: 43
<212> TYPE: DNA
<213> ORGANISM: Artificial Sequence
<220> FEATURE:
<223> OTHER INFORMATION: I-CeuI recognition site

<400> SEQUENCE: 5
agcggcccgt aactataacg gtcctaaggt agcgaaggcc gct                 43

<210> SEQ ID NO 6
<211> LENGTH: 43
<212> TYPE: DNA
<213> ORGANISM: Artificial Sequence
<220> FEATURE:
<223> OTHER INFORMATION: complement of I-CeuI recognition site

<400> SEQUENCE: 6
agcggccttc gctaccttag gaccgttata gttacgggcc gct                 43

<210> SEQ ID NO 7
<211> LENGTH: 51
<212> TYPE: DNA
<213> ORGANISM: Artificial Sequence
<220> FEATURE:
<223> OTHER INFORMATION: PI-PspI recognition site

<400> SEQUENCE: 7
agcggccaaa atcctggcaa acagctatta tgggtattat gggtggccgc t        51

<210> SEQ ID NO 8
<211> LENGTH: 51
<212> TYPE: DNA
<213> ORGANISM: Artificial Sequence
<220> FEATURE:
<223> OTHER INFORMATION: complement of PI-PspI recognition site

<400> SEQUENCE: 8
agcggccacc cataataccc ataatagctg tttgccagga ttttggccgc t        51

<210> SEQ ID NO 9
<211> LENGTH: 5916
<212> TYPE: DNA
<213> ORGANISM: Artificial Sequence
<220> FEATURE:
<223> OTHER INFORMATION: pcosKA5

<400> SEQUENCE: 9
gtaccgtcga ggtcgacccg taactataac ggtcctaagg tagcgaaggt cgacggtatc    60
gccacccata atacccataa tagctgtttg ccaggatttt gggataagct tgatccccct   120
cgaggtcgac ccgtaactat aacggtccta aggtagcgaa ggtcgacggt atcgccaccc   180

| | |
|---|---|
| ataatacccca taatagctgt tgccaggat tttgggataa gcttgatccc tatagtgagt | 240 |
| cgtattatgc ggccgcgaat tcttgaagac gaaagggcct cgtgatacgc ctatttttat | 300 |
| aggttaatgt catgataata atggtttctt agacgtcagg tggcactttt cggggaaatg | 360 |
| tgcgcggaac ccctatttgt ttatttttct aaatacattc aaatatgtat ccgctcatga | 420 |
| gacaataacc ctgataaatg cttcaataat attgaaaaag gaagagtatg agtattcaac | 480 |
| atttccgtgt cgcccttatt cccttttttg cggcattttg cttcctgttt ttgctcaccc | 540 |
| agaaacgctg gtgaaagtaa aagatgctga agatcagttg ggtgcacgag tgggttacat | 600 |
| cgaactggat ctcaacagcg gtaagatcct tgagagtttt cgccccgaag aacgttttcc | 660 |
| aatgatgagc acttttaaag ttctgctatg tggcgcggta ttatcccgtg ttgacgccgg | 720 |
| gcaagagcaa ctcggtcgcc gcatacacta ttctcagaat gacttggttg agtactcacc | 780 |
| agtcacagaa aagcatctta cggatggcat gacagtaaga gaattatgca gtgctgccat | 840 |
| aaccatgagt gataacactg cggccaactt acttctgaca acgatcggag gaccgaagga | 900 |
| gctaaccgct tttttgcaca acatggggga tcatgtaact cgccttgatc gttgggaacc | 960 |
| ggagctgaat gaagccatac caaacgacga gcgtgacacc acgatgcctg cagcaatggc | 1020 |
| aacaacgttg cgcaaactat taactggcga actacttact ctagcttccc ggcaacaatt | 1080 |
| aatagactgg atggaggcgg ataaagttgc aggaccactt ctgcgctcgg cccttccggc | 1140 |
| tggctggttt attgctgata aatctggagc cggtgagcgt gggtctcgcg gtatcattgc | 1200 |
| agcactgggg ccagatggta agccctcccg tatcgtagtt atctacacga cggggagtca | 1260 |
| ggcaactatg gatgaacgaa atagacagat cgctgagata ggtgcctcac tgattaagca | 1320 |
| ttggtaactg tcagaccaag tttactcata tatactttag attgatttaa aacttcattt | 1380 |
| ttaatttaaa aggatctagg tgaagatcct tttgataat ctcatgacca aaatccctta | 1440 |
| acgtgagttt cgttccact gagcgtcaga ccccgtagaa aagatcaaag gatcttcttg | 1500 |
| agatccttt tttctgcgcg taatctgctg cttgcaaaca aaaaaaccac cgctaccagc | 1560 |
| ggtggtttgt ttgccggatc aagagctacc aactcttttt ccgaaggtaa ctggcttcag | 1620 |
| cagagcgcag ataccaaata ctgtccttct agtgtagccg tagttaggcc accacttcaa | 1680 |
| gaactctgta gcaccgccta catacctcgc tctgctaatc ctgttaccag tggctgctgc | 1740 |
| cagtggcgat aagtcgtgtc ttaccggggtt ggactcaaga cgatagttac cggataaggc | 1800 |
| gcagcggtcg ggctgaacgg ggggttcgtg cacacagccc agcttggagc gaacgaccta | 1860 |
| caccgaactg agatacctac agcgtgagct atgagaaagc gccacgcttc cgaagggaga | 1920 |
| aaggcggaca ggtatccggt aagcggcagg gtcggaacag gagagcgcac gagggagctt | 1980 |
| ccagggggaa acgcctggta tctttatagt cctgtcgggg tttcgccacc tctgacttga | 2040 |
| gcgtcgattt tgtgatgct cgtcaggggg gcggagccta tggaaaaacg ccagcaacgc | 2100 |
| ggccttttta cggttcctgg ccttttgctg gccttttgct cacatgttct ttcctgcgtt | 2160 |
| atcccctgat tctgtggata accgtattac cgcctttgag tgagctgata ccgctcgccg | 2220 |
| cagccgaacg accgagcgca gcgagtcagt gagcgaggaa gcggaagagc gctgacttcc | 2280 |
| gcgtttccag actttacgaa acacggaaac cgaagaccat tcatgttgtt gctcaggtcg | 2340 |
| cagacgtttt gcagcagcag tcgcttcacg ttcgctcgcg tatcggtgat tcattctgct | 2400 |
| aaccagtaag gcaaccccgc cagcctagcc gggtcctcaa cgacaggagc acgatcatgc | 2460 |
| gcacccgtca gatccagaca tgataagata cattgatgag tttggacaaa ccacaactag | 2520 |
| aatgcagtga aaaaaatgct ttatttgtga aatttgtgat gctattgctt tatttgtaac | 2580 |

```
cattataagc tgcaataaac aagttaacaa caacaattgc attcatttta tgtttcaggt      2640 tcaggggag gtgtgggagg ttttttaaag caagtaaaac ctctacaaat gtggtatggc      2700
tgattatgat ctctagtcaa ggcactatac atcaaatatt ccttattaac ccctttacaa      2760
attaaaaagc taaaggtaca caattttttga gcatagttat taatagcaga cactctatgc      2820
ctgtgtggag taagaaaaaa cagtatgtta tgattataac tgttatgcct acttataaag      2880
gttacagaat attttttccat aattttcttg tatagcagtg cagcttttc ctttgtggtg      2940 taaatagcaa agcaagcaag agttctatta ctaaacacag catgactcaa aaacttagc      3000 aattctgaag gaaagtcctt gggtcttct acctttctct tctttttgg aggagtagaa      3060 tgttgagagt cagcagtagc ctcatcatca ctagatggca tttcttctga gcaaaacagg      3120
ttttcctcat taaaggcatt ccaccactgc tcccattcat cagttccata ggttggaatc      3180
taaaatacac aaacaattag aatcagtagt ttaaacatt atacacttaa aaattttata      3240
tttaccttag agctttaaat ctctgtaggt agtttgtcca attatgtcac accacagaag      3300
taaggttcct tcacaaagat ccggaccaaa gcggccatcg tgcctcccca ctcctgcagt      3360 tcggggcat ggatgcgcgg atagccgctg ctggttcct ggatgccgac ggatttgcac      3420
tgccggtaga actcgcgagg tcgtccagcc tcaggcagca gctgaaccaa ctcgcgaggg      3480
gatcgagccc tcgacgctct cccttatgcg actcctgcat taggaagcag cccagtagta      3540
ggttgaggcc gttgagcacc gccgccgcaa ggaatggtgc atgcaaggag atggcgccca      3600
acagtccccc ggccacgggc ctgccaccat acccacgccg aaacaagcgc tcatgagccc      3660
gaagtggcga gcccgatctt ccccatcggt gatgtcggcg atataggcgc cagcaaccgc      3720
acctgtggcg ccggtgatgc cggccacgat gcgtccggcg tagaggatct tggcagtcac      3780
agcatgcgca tatccatgct tcgaccatgc gctcacaaag taggtgaatg cgcaatgtag      3840
tacccacatc gtcatcgctt tccactgctc tcgcgaataa agatggaaaa tcaatctcat      3900
ggtaatagtc catgaaaatc cttgtattca taaatcctcc aggtagctat atgcaaattg      3960
aaacaaaaga gatggtgatc tttctaagag atgatggaat ctcccttcag tatcccgatg      4020
gtcaatgcgc tggatatggg atagatggga atatgctgat ttttatggga cagagttgcg      4080
aactgttccc aactaaaatc attttgcacg atcagcgcac tacgaacttt acccacaaat      4140
agtcaggtaa tgaatcctga tataaagaca ggttgataaa tcagtcttct acgcgcatcg      4200
cacgcgcaca ccgtagaaag tctttcagtt gtgagcctgg gcaaaccgtt aactttcggc      4260
ggctttgctg tgcgacaggc tcacgtctaa aaggaaataa atcatgggtc ataaaattat      4320
cacgttgtcc ggcgcggcga cggatgttct gtatgcgctg ttttccgtg gcgcgttgct      4380 gtctggtgat ctgccttcta aatctggcac agccgaattg cgcgagcttg gttttgctga      4440
aaccagacac acagcaactg aataccagaa agaaaatcac tttacctttc tgacatcaga      4500
agggcagaaa tttgccgttg aacacctggt caatacgcgt tttggtgagc agcaatattg      4560
cgcttcgatg acgcttggcg ttgagattga tacctctgct gcacaaaagg caatcgacga      4620
gctggaccag cgcattcgtg acaccgtctc cttcgaactt attcgcaatg gagtgtcatt      4680
catcaaggac gccgctatcg caaatggtgc tatccacgca gcggcaatcg aaacacctca      4740
gccggtgacc aatatctaca acatcagcct tggtatccag cgtgatgagc cagcgcagaa      4800
caaggtaacc gtcagtgccg ataagttcaa agttaaacct ggtgttgata ccaacattga      4860
aacgttgatc gaaaacgcgc tgaaaaacgc tgctgaatgt gcggcgctgg atgtcacaaa      4920
```

-continued

```
gcaaatggca gcagacaaga aagcgatgga tgaactggct tcctatgtcc gcacggccat    4980
catgatggaa tgtttccccg gtggtgttat ctggcagcag tgccgtcgat agtatgcaat    5040
tgataattat tatcatttgc gggtcctttc cggcgatccg ccttgttacg gggcggcgac    5100
ctcgcgggtt ttcgctattt atgaaaattt tccggtttaa ggcgtttccg ttcttcttcg    5160
tcataactta atgtttttat ttaaaatacc ctctgaaaag aaaggaaacg acaggtgctg    5220
aaagcgagct ttttggcctc tgtcgtttcc tttctctgtt tttgtccgtg gaatgaacaa    5280
tggaagtcaa caaaaagcag ctggctgaca ttttcggtgc gagtatccgt accattcaga    5340
actggcagga cagggaatg cccgttctgc gaggcggtgg caagggtaat gaggtgcttt     5400
atgactctgc cgccgtcata aaatggtatg ccgaaaggga tgctgaaatt gagaacgaaa    5460
agctgcgccg ggaggttgaa gaactgcggc aggccagcga ggcagatcca caggacgggt    5520
gtggtcgcca tgatcgcgta gtcgatagtg gctccaagta gcgaagcgag caggactggg    5580
cggcggcaaa gcggtcggac agtgctccga gaacgggtgc gcatagaaat tgcatcaacg    5640
catatagcgc tagcagcacg ccatagtgac tggcgatgct gtcggaatgg acgatatccc    5700
gcaagaggcc cggcagtacc ggcataacca agcctatgcc tacagcatcc agggtgacgg    5760
tgccgaggat gacgatgagc gcattgttag atttcataca cggtgcctga ctgcgttagc    5820
aatttaactg tgataaacta ccgcattaaa gcttatcgat gataagcggt caaacatgag    5880
aattcgcggc cgcaattaac cctcactaaa ggatcc                              5916
```

METHODS AND MATERIALS FOR THE RAPID AND HIGH VOLUME PRODUCTION OF A GENE KNOCK-OUT LIBRARY IN AN ORGANISM

CROSS REFERENCE TO RELATED APPLICATIONS

This application is a continuation in part of copending U.S. patent application Ser. No. 09/728,194. filed Nov. 30, 2000 which is a continuation of U.S. patent application Ser. No. 09/270,620, filed Mar. 17, 1999. PCT/US00/07317 filed Mar. 16, 2000 is a continuation of U.S. patent application Ser. No. 09/270,620, filed Mar. 17, 1999. The contents of which are incorporated by reference.

FIELD OF THE INVENTION

The present invention relates to methods and materials, such as vectors, for the systematic and random insertion of genetic material into the genome of an organism.

BACKGROUND

The present invention relates to methods and materials for the systematic and random insertion of genetic material into the genome of an organism. The invention allows the rapid mutagenesis of organisms to mutate essentially every gene of an organism, particularly fungi, and allow the reliable and efficient identification of the gene being knocked out in each mutagenesis event. The invention also facilitates very high efficiency of homologous recombination, particularly in species, such as filamentous fungi, that have previously been notorious for low frequency of such events.

Numerous methods for introducing foreign genetic material into living cells have become routine since the first instances of genetic engineering almost a quarter century ago. Introduction of foreign genetic material can be into the cell via a vector that may replicate or by incorporation into the genome of the host cell. The introduction of such foreign genetic material has allowed the expression of a protein in a species that usually does not produce the protein. It has also allowed the regulation of the expression of a protein (overexpression and underexpression) by introducing modified regulatory sequences making the transcription and translation of the protein more or less efficient. Another use for genetic engineering has been the modification of the biological activity of a structural protein or enzyme by altering the coding region of a gene and thus altering the amino acid sequence of the protein produced. The altered amino acid sequence can lead to changes in conformation, changes in surface charge, and changes in the higher structure of the protein (tertiary and quanternary structure) which all can lead to changes in biological activity.

With the recent growth of the field of "functional genomics" out of the discipline of genomics or gene sequencing, the manipulation of DNA in organisms has taken on another urgent task. In addition to sequencing the genetic material of an organism, functional genomics seeks to identify the function of the genes of a target organism on an industrial scale. By determining the function of most, if not all, genes and the products of those genes in an organism, functional genomics can accelerate the identification of gene and protein targets and allow the identification of compounds that will modulate those genes and gene products to alleviate disease, improve human and animal health, and improve the quality and quantity of food crops. To achieve this, it is necessary to develop rapid, high volume techniques for sytematically altering the expression of essentially every gene in an organism, identifying the corresponding gene and monitoring the effect of the gene alteration on the phenotype of the organism.

Automated processes in molecular genetics have allowed the systematic analysis of genomes from microorganisms, such as yeast and bacteria, by DNA sequencing. Attention is focused on rapidly ascribing functions to newly discovered genes. It is widely recognized in the field of genetics that gene function is most desirably assigned through the analysis of organisms containing defined gene mutations (mutants).

Previous methods of introducing genetic material into a eukaryotic organism are sufficient for mutating a single gene. Such methods include protoplast fusion, transformation by electroporation, particle bombardment, chemical perturbation of cellular envelopes (membranes and walls), phage and viral infection, transduction and physical insertion of DNA into cells. Many of these methods are limited to introducing DNA into a cell in the form of a vector, where the DNA is expressed to produce its gene product. The desired characteristics of a useful gene insertion method for functional genomics include the insertion of a gene or DNA fragment into essentially every gene of the genome of the target organism in an efficient and systematic manner. However, the majority of methods for inserting DNA into the genome of an organism are not target specific. Methods for targeted integration of DNA into a specific location in the genome of an organism are less reliable and often have low efficiency. Accordingly, there is a need for efficient methods for site specific integration of DNA into the genome of an organism.

One method for the site specific insertion of DNA into another piece of DNA, including genomic DNA, involves the use of viral integration systems, such as Crelox (Sauer (1996) Nucleic Acid Res. 24:4608–4613) and Flp recombinase (Seibler and Bode (1997) Biochemistry 36:1740–1747). These systems insert DNA at specific sites in DNA in genomic DNA of a host, but those specific sites must first be randomly engineered into the genome. Recently, the ability of enzymes known as transposases to transfer DNA fragments from one location in DNA into another random location in DNA have been discovered (Devine et al., U.S. Pat. No. 5,677,170; Devine et al., U.S. Pat. No. 5,728,551; Hackett et al., WO 98/40510; Plasternak et al., WO 97/29202; Reznikoff et al., WO 98/10077; Craig WO 98/37205; Strathman et al., (1991) Proc. Nat. Acad. Sci. USA 88:1247–1250; Phadnis et al., (1989) Proc. Nat. Acad. Sci. USA 86:5908–5912; Way et al., (1984) Gene 32:269–279; Kleckner et al., (1991) Method. Enzymol. 204:139–180; Lee et al., (1987) Proc. Nat. Acad. Sci. USA 84:7876; Brown et al. (1987) Cell 49:347–356; Eichinger et al. (1988) Cell 54:955–966; Eichinger et al. (1990) Genes Dev. 4:324–330). Generally, a transposase recognizes a relatively short DNA sequence known as an inverted repeat that is located on the flanks of an internal piece of DNA. The DNA sequence comprising the internal DNA sequence and the two flanking internal repeat sequences is known as a transposon or transposable element. The transposase has the ability to excise the transposon and insert it in another piece of DNA into which it comes into contact. Typically, the location of the insertion is not totally random, but occurs preferentially at target sequence locations (so called "hot spots"; Kleckner et al., (1991) Method. Enzymol. 204:139–180). Like the viral systems, the insertions are site specific, but the sites are randomly located in the genome and do not allow site directed insertion.

One use for transposons has been to introduce a desired gene randomly into the organism's genome. Another use of transposons is as a sequencing tool since the sequence of the transposon is often known, especially at the borders, such that use of primers designed for the transposon would allow sequencing of the DNA into which the transposon is inserted. The lack of randomness in insertion location would detract from the use of transposons as tools to systematically sequence essentially all genes in an organism or to systematically knock out essentially all genes in an organism. Therefore, their use in functional genomics would appear to be limited.

Using transposons has thus far involved engineering the transposon into a plasmid (e.g., Reznikoff et al., WO 98/10077) and introducing the plasmid into a target organism such that the transposed gene is expressed by the plasmid (Devine et al., U.S. Pat. No. 5,677,170; Devine et al., U.S. Pat. No. 5,728,551). Alternatively, genetic material has been introduced into the genome of an organism by directly transferring the transposon from a plasmid to the genome of a target organism in the presence within the cell of the transferring transposase (Hackett et al., WO 98/40510; Plasternak et al., WO 97/29202). For this to occur, the interior of the cell to be transposed must include a transposable element on a plasmid and the corresponding transposase. Consequently, the only use of transposons to get DNA into the genome of an organism using a transposon has been to directly transpose the transposable DNA in the presence of a transposase into a site specific, but not site directed location (Hackett et al., WO 98/40510; Plasternak et al., WO 97/29202). Additionally, vectors containing a transposon event have been limited to plasmids and the use of the transposed vectors has been the expression of the transposed gene's protein. Moreover, the introduction of the transposon usually occurs at one of the hotspots, not randomly. The use of transposons to introduce DNA into filamentous fungi, and particularly to introduce DNA either directly or indirectly into the fungal genome has only recently been accomplished (Migheli et al. (1999) Genetics 15:1005–1013).

To accomplish site directed insertion of DNA into the genome of an organism, the method of homologous recombination is necessary, particularly when the objective of insertion is to mutate essentially every gene of the organism. However, there is a general difficulty in transforming filamentous fungal cells by homologous recombination. Such recombination has been notoriously inefficient.

Genome-wide mutagenesis is particularly problematic in filamentous fungi for several reasons. First, active and tractable endogenous transposons have not been described for the vast majority of filamentous fungi. Second, during DNA-transformation, homologous recombination occurs less frequently than nonhomologous (illegitimate or ectopic) recombination. During ectopic recombination, the introduced DNA construct does not recombine with its homologous genome segment but recombines at varied sites throughout the genome. Thus, in a resultant group of transformants, strains containing site directed mutations such as gene knockouts (KO's) as a result of homologous recombination must be identified against a large background of strains containing ectopic (nonhomologous) recombination events. Finally, large homologous chromosomal DNA regions (>1000 bp) are needed to direct homologous recombination. Thus several rounds of standard recombinant DNA technology (digestion of DNA with restriction enzymes, isolation of DNA fragments, ligation into plasmid vectors, transformation of E. coli and screening of bacterial colonies) are needed to assemble a single gene KO vector construct. This requirement is detrimental to efficient automation.

Filamentous fungi are a large and diverse group within the kingdom Mycota. They impact human health as important recyclers of terrestial biomass, as hosts for industrial chemical, vitamin, enzyme and pharmaceutical production, as agents of deterioration and decay and as pathogens of plants and animals. This group of organisms are generally regarded as distinct from distantly-related unicellular fungi such as the yeast *Saccharomyces cerevisiae*. This distinction is obvious in terms of growth morphology (multicellular filamentous hyphae as opposed to unicellular buds) and metabolism (e.g., *S. cerevisiae* is a facultative anaerobe whereas filamentous fungi are strictly aerobic). The systematic analysis and assignment of function to all the genes of filamentous fungi and other eukaryotes would provide much new and valuable information about these important organisms.

SUMMARY OF THE INVENTION

The present invention provides techniques and materials to allow the systematic mutation of essentially all genes in a eukaryotic organism, especially a filamentous fungus, by facilitating the homologous recombination of all the genes of the organism. Homologous recombination is facilitated by the large insert vector libraries (e.g., cosmid, BAC, etc.) as a substrate for transposon mediated mutagenesis of the genomic DNA carried by the vector. The use of a large insert vector, such as a cosmid, which is capable of containing large inserts of cloned DNA, allows large flanking DNA sequences that are homologous to genomic DNA on each side of the inserted transposon. Optionally, the genomic DNA sequences that flank the transposon can then be sequenced using primers targeted to the ends of the inserted transposon. The large genomic sequences that flank the transposon allow for increased frequencies of homologous recombination with the genome of the target eukaryotic organism, especially in species where homologous recombination efficiency has previously been low. Transposon mediated mutagenesis of cosmids is not recommended by manufacturers of commercially available transposon systems. Therefore, the present invention uses new methods and materials to solve the problem of homologous recombination of difficult species and the rapid, large scale production of genomic mutants as well as the routine sequencing of the gene being mutated. The present invention allows the industrialization of both the identification of essentially all genes in an organism as well as the assignment of function to each of those genes by analysis of the corresponding genomic mutation.

Thus, in one aspect, the present invention provides a method for facilitating site directed homologous recombination in a eukaryotic organism to produce mutants comprising:

1) providing at least one cosmid, wherein said cosmid comprises a first vector and genomic DNA from a target eukaryotic organism and wherein said first vector is not more than 6.4 kb in length and comprises a first selectable marker functional for selection in bacteria;

2) providing a second vector comprising a transposable element, said transposable element comprising a nucleotide sequence coding for a second selectable marker flanked on each side by an inverted repeat sequence, wherein said second selectable marker is bifunctional for selection in bacteria and in the target organism, and wherein said inverted repeat sequences are functional as a binding site for a transposase;

3) incubating at least one of said cosmids with said second vector in vitro, in the presence of a transposase specific for the inverted repeat sequences on said second vector, such that said transposable element transposes into said genomic DNA to produce a disrupted cosmid;

4) amplifying said disrupted cosmid in a bacterial cell and selecting for the presence of said first and second selectable markers in said bacterial cell;

5) introducing the disrupted cosmid amplified in step 4) into a target cell from said target organism so that homologous recombination can occur between said genomic DNA in said disrupted cosmid and the genome of said target organism and thereby produce a mutated target cell; and 6) selecting for the presence of said second selectable marker and screening for successful homologous recombination produced by step 5) in said mutated target cell.

Minimal plasmid vectors are provided for use in the generation of large insert libraries, particularly for use in cloning large fragments of DNA, such as are found in genomic DNA samples. The vectors of the invention comprise an origin of replication for bacterial cells, a selectable marker gene for bacterial cells, a bacteriophage packaging site, and a multiple cloning site comprising recognition sites for one or more rare-cutting restriction endonucleases, which endonucleases preferably include one or more homing endonucleases. The vectors are less than about 6.5 kb in length, and may be less than about 2.3 kb in length. In a preferred embodiment of the invention, the large insert vector library is a cosmid library or a BAC library, more preferably a cosmid library. Preferred cosmid vectors are pcosKA5, pcosJH1 and pPGFRKA1 (pcosKA4).

In a preferred embodiment of the invention, said transposable element and transposase are systems of Himar1, AT-2, GPS-1, GPS-2, Himar1, EZ::tn, SIF or Mu.

The most preferred embodiment of the invention relates to homologous recombination in filamentous fungi, particularly *Magnaporthe grisea, Magnaporthe graminicola, Botrytis cinerea, Erysiphe graminis, Aspergillus niger, Aspergillus fumigatus* or *Phytophthora infestans*.

DETAILED DESCRIPTION OF INVENTION

Definitions:

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are herein incorporated by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a primer" includes a plurality of such primers and reference to "a recognition site" includes reference to one or more recognition sites and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Minimal bacteriophage packaging site. A sequence of the cohesive end of lambda and "cos end" or "open cos site" means a 5'-end overhang of λ DNA containing a 12 base sequence: 5' GGGCGGCGACCT 3'(SEQ ID NO:1). Cosmid and lambda phage-based cloning vectors include a nucleotide sequence termed the "cos site" which provides a signal for packaging the nucleic acid into a lambda phage particle. Both cosmids and lambda vectors utilize the cos site and therefore share the cloning efficiency afforded lambda phage-based cloning systems.

The 12 bp cohesive ends at each end of the lambda genome (cos sites) are recognized by lambda proteins and the DNA between two cos sites is cleaved from the concatamer coincident with its packaging into a single prohead. The cleavage product is a linear DNA molecule of unit genome size with complementary single-stranded cohesive ends. The remaining head proteins then assemble and the tail, which has been assembled independently, attaches to the head to form an intact infectious phage.

In one embodiment, the present invention is not limited to the use of the cos site as the minimal packaging signal. Other bacteriophage systems have been described that define the packaging of phage DNA into the phage particle by a packaging site. For example, the pac sequence for bacteriophage P1 has been characterized and functions as a site that initiates packaging of DNA into the bacteriophage P1 particle (Sternberg et al. (1990) P.N.A.S. 87:8070–8074). The minimum nucleotide sequence required to function as a pac site is 162 nucleotides in length. The 162 nucleotide sequence defining the bacteriophage P1 pac site can be used in place of the cos site to produce a cloning vector according to the methods of the present invention. This vector is packaged into P1 bacteriophage particles using a P1 packaging extract. Bacteriophage P1 particles can accommodate up to 102 kb of genomic DNA before the particle head is full. Thus pac cloning systems based on bacteriophage P1 can be produced according to the present methods that have an even greater cloning capacity than those based on bacteriophage lambda.

Origin of replication. Vectors of the invention comprise an origin of replication that is functional in a bacterial cell, and that maintains the vector as multiple copies in the cell, preferably at a medium to low copy number. The origin can be chosen from vectors known in the art to have these characteristics in the selected bacterial host cell. Such vectors include, but are not limited to, pBR322, Col1, pMB1, p15A, pSC101, pACYC, pUC and the like. Suitable host cell species include *E. coli* and other gram negative rods, such as Pseudomonas, Erwinia, Shigella, Salmonella, Proteus, Klebsiella, Enterobacter and Yersinia, etc.

Plasmid copy number is determined primarily by the region of DNA surrounding and including the origin of replication in the plasmid. This region, known as the replicon, controls the initiation of plasmid replication. Plasmids derived from pBR322 contain the ColE1 origin of replication from pMB1. This origin of replication is tightly controlled, resulting in approximately 25 copies of the plasmid per bacterial cell. Plasmids derived from pUC contain a mutated version of the ColE1 origin of replication, which results in reduced replication control and approximately 500–700 plasmid copies per cell.

Selectable marker. The vectors will include an expressed gene encoding a selectable marker, e.g. antibiotic resistance; genes or operons that complement a metabolic defect of the bacterial host; resistance to phage infection, etc. Typically such markers encode resistance to an antibiotic or other drug. When bacteria transformed with the vector are grown in the presence of the drug, only those cells comprising the vector are able to survive. Many selectable markers are well-characterized and known in the art, e.g. resistance to ampicillin (β-lactamase); chloramphenicol (chloramphenicol acetyl transferase); kanamycin, streptomycin; tetracycline; etc.

Multiple cloning site: The vectors of the invention comprise a multiple cloning site, in which one or more recognition sequences for restriction endonucleases are present, and where the cleavage by the cognate restriction enzymes will not interrupt essential plasmid functions, including the packaging site, origin of replication, or selectable marker. At least one of the restriction endonuclease sites will be a site for a rare cutting enzyme. Rare cutting enzymes may be defined as enzymes that do not cut the target DNA on average more than 1 site in about $10^4$ bases of DNA, and may have on average not more than 1 site in about $5\times10^4$ bp DNA, or in about $10^5$ bp DNA. It will be understood by one of skill in the art that due to a random distribution of sites, some fragments will be substantially larger than average, and some will be substantially smaller. The frequency of cutting for a particular enzyme is determined in part by the length of the recognition sequence, but is also determined by the distribution of bases and motifs in the target DNA, and thus what is a rare cutter in one organism may cut more frequently in another organism. Restriction enzymes of interest as rare cutters include NotI, Pme I, Ksp I, Sfi 1 and other restriction enzymes having a recognition site of at least 8 bp.

Of particular interest as rare cutting enzymes such as homing endonucleases, which are intron or intein encoded, and have a recognition sequence of 12–40 bp (see Belfort et al. (1997) Nucleic Acid Res. 25:3379–3388). The cleavage site leaves 3' and 5' overhangs of 1–10 bases. Examples of homing endonucleases include-Ppo I; I-Ceu I; I-Dmo I; I-Sce I; PI-Sce I; PI-Psp I; and the like (see U.S. pat. Nos. 5,420,032 and 6,096,523, the contents of which are incorporated by reference; and New England Biolabs catalog, edition current at the time of filing). Preferred vectors comprise at least one homing endonuclease recognition sequence.

Embodiments of the Invention

Gene function analysis in eukaryotic organisms has typically been performed by gene disruption followed by observation of phenotypic changes. This process traditionally involves construction of a disruption vector and in vivo gene disruption by endogenous homologous recombination of the disruption vector with the genome of the target organism.

A typical prior art gene disruption experiment required the construction of a disruption vector comprising a DNA fragment homologous to the target gene, wherein this DNA fragment is disrupted by the insertion of a selectable marker. The prior art used restriction enzyme technology to disrupt large insert vectors. Such methods require multiple steps of cloning and analysis. Furthermore, sequence information (DNA sequence or a restriction map) was required for each gene that was to be disrupted. The disruption vector was then introduced into a cell from a target organism and endogenous homologous recombination resulted in the introduction of the selectable marker into the target gene. In contrast, the methods use in vitro transposition of a bifunctional marker into a large insert vector containing genomic DNA in order to create the disrupted vectors for use in homologous recombination.

Transposition can be induced in a host-independent, cell-free system by a simple reaction including recipient DNA, a transposon and the corresponding transposase. In vitro transposition technology has been applied to the mapping and sequencing of genomic DNA, gene expression and localization, and genome scanning, but never before to systematic chromosomal gene disruption studies in eukaryotes.

The present invention has greatly improved this process and transformed gene function analysis into a high throughput genome-scale approach. Transposon Arrayed Gene Knock-Out (TAG-KO) technology combines transposomics, bioinformatics and recombination methodologies. In the methods of the invention, a transposon carrying a bi-functional selectable marker transposes into recipient cosmid libraries or other large insert vector library in vitro to create disrupted large insert vectors. Because the disruption vector is created using transposons, no prior knowledge of the sequence or the restriction map of the genomic target DNA present in the vector is needed. Furthermore, in contrast to prior art methods involving the use of restriction enzyme technology to create a mutation in genomic DNA contained in an individual vector, the methods of the invention may be used to create transposon mutations simultaneously in an entire library of large insert genomic vectors. (If desired, the genomic DNA flanking the site where the transposon inserted can then be sequenced using primers that face outwards from each end of the transposon. This sequence information may then be used for gene discovery.) The disrupted large insert vectors containing a target gene with a transposon insertion are then used for gene disruption in a cell from a target eukaryotic organism. The use of a vector capable of carrying a large genomic insert increases the likelihood for cloning of entire genes and gene clusters, and improves the homologous recombination rate. The simultaneous production and characterization of thousands of gene disruption vectors accompanied by high levels of homologous recombination defines a new and unique tool for effective large scale gene function analysis in eukaryotes, and in filamentous fungi in particular.

In a preferred embodiment, TAG-KO consists of 3 major steps: 1) Large-scale disruption vector production by in vitro transposition into large insert vector libraries by a transposon carrying a bifunctional marker selectable in both a prokaryote and the target organism. 2) Determination of target sequence by sequencing using primers facing outwards from each end of the transposon. 3) In vivo disruption of the genome of a target organism by introduction of the disrupted large insert vector into a target cell followed by selection for the bifunctional marker and phenotype analysis. The traditional and time-consuming process of disruption vector production via restriction enzyme technology has been eliminated, and the frequency of homologous recombination has been increased significantly by the use of cosmid disruption vectors.

The present invention relates to a method for facilitating site directed homologous recombination in a eukaryotic organism to produce mutants comprising:

1) providing at least one cosmid, wherein said cosmid comprises a first vector and genomic DNA from a target eukaryotic organism and wherein said first vector is not more than 6.4 kb in length and comprises a first selectable marker functional for selection in bacteria;

2) providing a second vector comprising a transposable element, said transposable element comprising a nucleotide sequence coding for a second selectable marker flanked on each side by an inverted repeat sequence, wherein said second selectable marker is bifunctional for selection in bacteria and in the target organism, and wherein said inverted repeat sequences are functional as a binding site for a transposase;

3) incubating at least one of said cosmids with said second vector in vitro, in the presence of a transposase specific for the inverted repeat sequences on said second vector, such that said transposable element transposes into said genomic DNA to produce a disrupted cosmid;

4) amplifying said disrupted cosmid in a bacterial cell and selecting for the presence of said first and second selectable markers in said bacterial cell;

5) introducing the disrupted cosmid amplified in step 4) into a target cell from said target organism so that homologous recombination can occur between said genomic DNA in said disrupted cosmid and the genome of said target organism and thereby produce a mutated target cell; and 6) selecting for the presence of said second selectable marker and screening for successful homologous recombination produced by step 5) in said mutated target cell.

Figure 2:
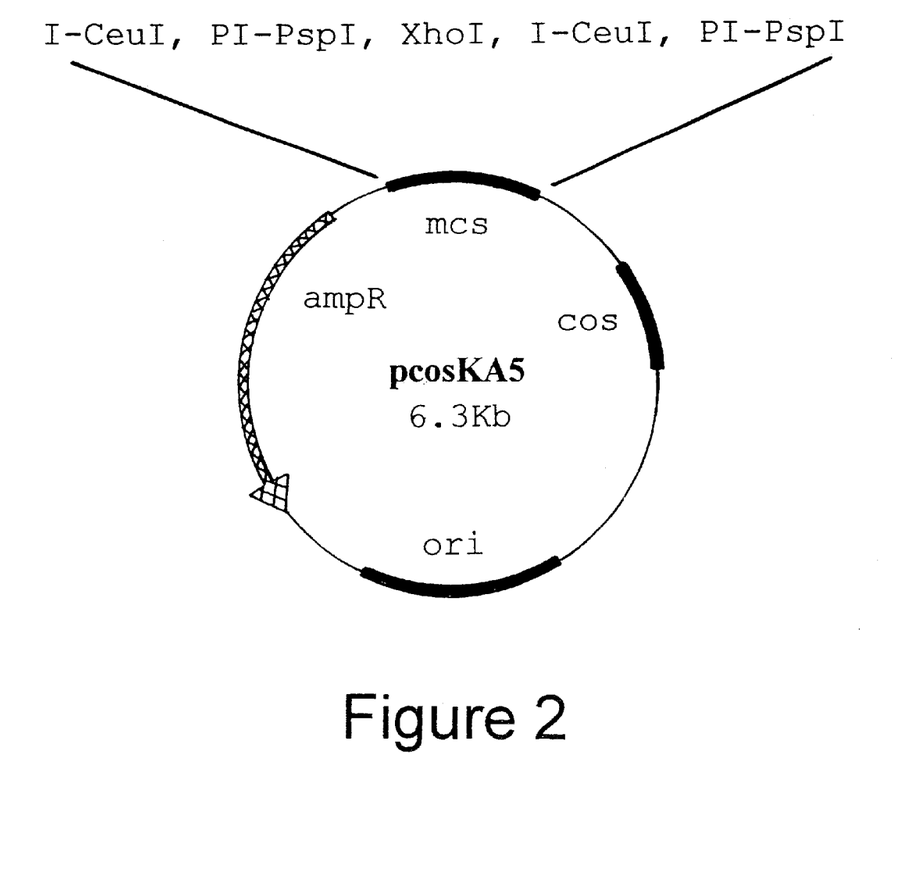
FIG. 2 is a schematic of the cosmid vector pcosKA5.
Figure 3:
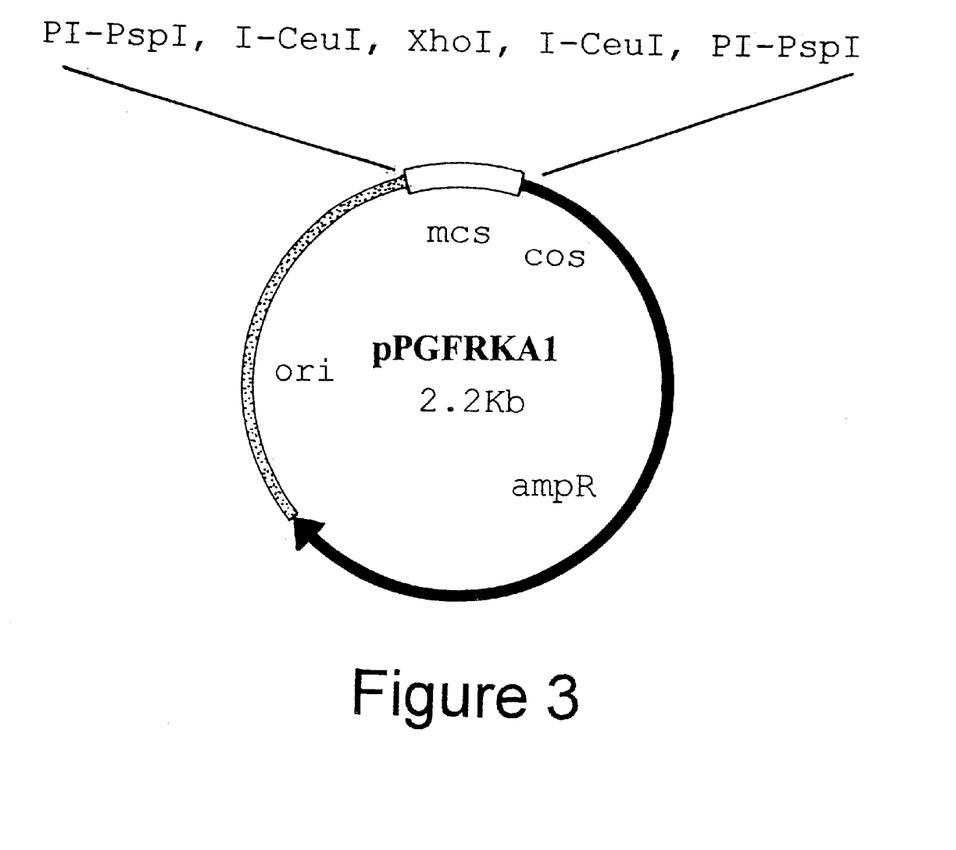
FIG. 3 is a schematic of the cosmid vector pPGFRKA1.

Preferably, the first vector is not more than 6.3 kb in length, or less than 2.3 kb in length. In preferred embodiments, the first vector is pcosJH1 (FIG. 1), pcosKA5 (FIG. 2) or pPGFRKA1 (FIG. 3). Most preferably the first vector is pcosKA5. Preferred first vectors will contain a recognition site for at least one homing endonuclease. Most preferably, the recognition site is for I-CeuI and/or PI-PspI homing endonucleases. The recognition sites for these and other restriction enzymes are known to those skilled in the art.

In preferred embodiments, said cosmid contains at least 30, 35, 40, 45, 50, or 52 kilobase pairs of genomic DNA from a target organism.

The present invention is a method for facilitating site-directed homologous recombination in an organism to produce mutations at the directed site. Homologous recombination occurs when two pieces of DNA having similar sequences exchange a portion or fragment of their length of similar DNA sequence through a cross-over event. In particular, the two portions or fragments of DNA involved in the homologous recombination preferably have similar or nearly identical DNA sequences at the ends or distal regions of the portion or fragment of DNA that is exchanged. Mutations are any change that alters the sequence of the nucleotide bases in the genetic material (DNA) of an organism or cell, with alteration occurring either by displacement, addition, deletion, or other destruction. The alteration to the DNA sequence would alter its meaning, that is, its ability to produce the normal amount or normal kind of protein, so the organism or cell itself is altered. Such an altered organism or cell is called a mutant. The most desirable mutations for purposes of the present invention are mutations that cause a decrease or increase in the biological activity of the gene product of the gene comprising the altered DNA. A particularly preferred mutant is a knock-out mutant that essentially destroys biological activity of the gene product through a null mutation or loss of transcription of the gene. Such a mutation can occur by inserting into the DNA of the gene of interest another piece of DNA, such that the inserted DNA disrupts the transcription of the normal gene or produces an incomplete transcript, resulting in a biologically inactive gene product or no gene product at all.

Construction of Large Insert Vectors and Vector Libraries

One step in the method of the present invention is the construction of a large insert vector containing a piece of DNA, the DNA comprising multiple genes from an organism and a first selectable marker functional for selection in an amplification host, preferably bacteria. Such a large insert vector can be any large vector (i.e., double stranded DNA capable of replication), including cosmids, λ vectors, artificial chromosomes, preferably bacterial artificial chromosomes (BACs), large plasmids, preferably large plasmids containing 5–10 kbp of inserted DNA fragment. The construction of cosmid or BAC libraries is preferred.

Cosmids are plasmid vectors designed for cloning large fragments of DNA. A cosmid is a plasmid containing a cos site from a bacteriophage. The cos site allows the plasmid to be packaged into the head of the bacteriophage. The resulting bacteriophage can then be used to introduce the cosmid into a bacterial host cell.

Large (~30–49 kb) foreign DNA fragments can be cloned using such vectors in an in vitro packaging reaction. Linearized vector DNA and insert DNA are co-ligated into concatamers, then packaged into phage heads with a packaging extract. Wherever two cos sites are separated by 38–53 kbp in the concatamer they, and the intervening DNA, are excised and packaged into an "infectious" phage that will efficiently inject its DNA contents into a bacterial cell. Once inside the cell, the DNA circularizes by annealing of its cohesive cos ends and then replicates as a large plasmid. Packaging and "infection" by phage lambda extracts makes cosmids nearly as efficient cloning vectors as lambda itself; suitable for construction of libraries from large genomes. Since cosmids rely on exogenously supplied protein extracts for packaging, these vectors are analogous to other helper-dependent, replication-defective virus vector systems. Using cosmid vectors is beneficial, because it allows larger pieces of genomic DNA to be cloned than with a lambda vectors. And because the vectors contain a conventional plasmid origin of DNA replication and selectable marker(s), they can be readily propagated and analyzed in E. coli.

Cosmid vectors are limited in the size of the insert that they can accept. This limitation is based on the packaging requirements of the bacteriophage head. For example, bacteriophage λ will only package DNAs into phage heads if the size is between 78% to 105% of the length of the wild-type λ genome. Therefore, the DNA flanked between two cos sites will only be packaged into λ heads if it is between approximately 38 and 53 kb long.

A typical λ, cosmid vector is generally about 6–8 kb in size, and therefore can accept at a maximum, an insert of approximately 47–49 kb in length. In order to accommodate the maximum size of insert, it is preferable to have a vector that is of minimal size, usually not more than about 6.5 kb in length, and may be not more than about 2.3 kb in length. The removal of sequences that are not required for the function of the vector allows a smaller size. While it is known that cosmid vectors must contain a plasmid origin of replication, a selectable marker, a cos site and a restriction site for cloning, the minimal sequences necessary for cosmid vector function have not previously been determined.

Markers that are functional for selection in bacteria and the source of such markers are known in the art and include Ampicillin (Amp), Tetracyclin (Tet), Chloramphenicol, Kanamycin (Kan), etc. Construction of a large insert vector begins with a vector, an autonomously replicating DNA unit into which DNA fragments are inserted. A vector contains operational genes including origins of replication, binding sites, restriction sites, etc. Preferably, the origin of replication is compatible with, and functional in, a cell such as *E. coli* for amplification, but is not compatible with or functional in the host organism which is the target of the homologous recombination. To the large insert framework is added an appropriate first selectable marker and a large fragment of DNA from an organism to be targeted for homologous recombination. A large fragment contains at least one entire gene from the target organism, more preferably multiple genes. As a gene typically has a length of about 3 kbp, the large fragment is preferably at least 5–10 kbp, more preferably more than 10 kbp in length. The longer the fragment of DNA inserted into the vector, the more likely that a mutated gene will have long lengths of flanking DNA to facilitate the homologous recombination.

The construction of many large insert vectors from a single organism will result in a gene library containing all the DNA of a given organism inserted as randomized inserted fragments into many thousands of different vectors. The most useful libraries are those containing genome insertions of the sizes needed to encompass complete genes, preferably multiple genes. The construction of a gene library may depend on the use of restriction enzymes like EcoRI that do not make too frequent cuts within DNA. Even then is may be preferably to use incompletely digested DNA when the desired genes are suspected of being extremely long. Additionally, large genomic insertions may be obtained by mechanically or physically shearing DNA of the target organism. Genomic fragments of at least 5 kilobase pairs (kbp) are very stably reproduced when inserted into plasmids. Larger fragments can be stably grown within specially tailored phage λ systems that require DNA inserts of 22 kbp in order to be packaged within mature particles. Even larger fragments can be stably inserted into cosmid vectors that can hold some 40 to 50 kbp of foreign DNA. Thus, using cosmids, for example, it would be possible to obtain multiple coverage of an entire organism genome within a manageable number of large insert vectors. For example, in many fungal genomes, 3000 large insert vectors would provide about a three fold coverage of the entire genome of the organism.

In another embodiment of the present invention, a large insert vector can include isolated large DNA fragments without vector operational genes. Such DNA fragments can be obtained by restriction digestion of genomic DNA, physical shearing of genomic DNA, PCR amplification of genomic DNA sections or any of the methods used to obtain a large fragment of DNA from an organism to be targeted for homologous recombination as described above. A large fragment contains at least one entire gene from the target organism, more preferably multiple genes. As a gene typically has a length of about 3 kbp, the large fragment is preferably at least 5–10 kbp, more preferably more than 10 kbp in length. The longer the fragment of DNA inserted into the vector, the more likely that a mutated gene will have long lengths of flanking DNA to facilitate the homologous recombination. A collection of many large DNA fragments from an organism results in a large DNA fragment library. Such a large DNA fragment library makes it possible to obtain multiple coverage of an entire organism genome within a manageable number of large DNA fragments.

Construction of Transposable Element

Another step in the method of the present invention is the construction of a second vector, preferably a plasmid, comprising a transposable element, said transposable element comprising a nucleotide sequence coding for a second selectable marker flanked on each side by an inverted repeat sequence, wherein said selectable marker is bifunctional for selection in bacteria and fungi and wherein said inverted repeat sequences are functional as a binding site for a transposase. The vector to be constructed need not be large and is therefore preferably a plasmid or of about plasmid size. This vector need not contain all the operational genes of a self replicating vector and can be produced by other amplification techniques using primers and polymerases. The vector will contain a bifunctional selectable marker flanked on each side by inverted repeat sequences that bind a transposase.

Transposons occur naturally as DNA sequences coding for an enzyme, transposase, that recognizes and cuts the DNA at sites flanking the gene for the transposase. Integrase is another form of transposase. The recognition sites, or binding sites for the transposase, are referred to as inverted repeat sequence. As such, transposable elements, when activated, produce an enzyme which promotes the excision of itself from one location in DNA and the insertion of the excised DNA at another site. As described in the prior art, the insertion location can be site specific at "hot spots." In the present invention, a bifunctional marker is inserted between the inverted repeat sequences, usually inactivating the production of viable transposase by the disrupted gene.

Usually, a transposable element can be obtained from a suitable source using restriction enzymes and a suitable bifunctional selectable marker can be inserted into the transposable element so long as the insertion does not disrupt the inverted repeat sequences that are the binding site for the appropriate transposon. Several such transposable elements are known in the art, including Himar1 (Lampe et al., (1998) Genetics 149:179–187), AT-2 (Perkin Elmer; Devine et al. (1997) Genome Res. 7:551–563), GPS-1 (New England Biolabs) or GPS-2 (New England Biolabs)

Suitable bifunctional selectable markers are selectable markers that are functional in both the amplification organism and the target organism for homologous recombination. In a preferred embodiment of the present invention, the amplification organism is a bacteria and the target organism for homologous recombination is filamentous fungi, such that a bifunctional selectable marker would allow selection in bacteria and filamentous fungi. Preferred selectable markers for the present invention include hygromycin, argB, pyr-4. Alternatively, a bifunctional selectable marker can include two individual selectable markers, one of which would allow selection in the amplification organism and the other would allow selection in the target organism for homologous recombination.

Transferring Transposable Element Randomly Into Large Insert Vector

After construction of the large insert vector library and construction of a transposable element as described above, they can be mixed or incubated with a suitable transposase such that the transposable element can be moved or transposed into the DNA of the large insert vector library in vitro. The conditions for accomplishing operation of the transposase to cause transposition of the transposable element into the large fragment of the large insert vector of the large insert vector library include use of a suitable transposase. A suitable transposase is a transposase that is specific for binding and excision of the DNA of the inverted repeat sequence being used in the transposable element. This is usually the transposase that is coded for by DNA that normally occurs within the borders of the inverted repeat sequence in its normal, unmutated condition. Particularly suitable transposases useful for the present invention as well as their corresponding transposable elements are the Himar1 mariner transposon (Lampe et al. (1998) Genetics 149:179–187; Lampe et al. (1996) EMBO J. 15:5470–5479), AT-2 (Perkin Elmer Corporation) and GPS-1 and GPS-2 (New England Biolabs). The suitable transposase is incubated with the large insert vector library and the transposable element for sufficient time and at sufficient temperature to allow transposition to take place. A suitable temperature is one that allows the enzymes to operate and not unfold or significantly change conformation, preferably from about 15° C. to about 45° C., more preferably from about 20° C. to about 30° C., most preferably about room temperature. The length of incubation will depend on the amount of coverage anticipated in the large insert vector library and the ratio of donor vector to target vector, the donor vector being the tranposable element and the target vector being the large insert vector. With a preferred ratio of about 1:1 donor:target, a suitable length of time for incubation will be less than about 12 hours, preferably about one hour.

In this way, each large insert vector of the large insert vector library will have the transposable element inserted somewhere in its large fragment DNA. This will result in a large insert vector that has been disrupted at one or more locations of the large fragment. As previously described, a large insert vector can also include just a large fragment DNA and a collection of large fragment DNA's can produce a large fragment DNA library. If the insertion occurs within a gene of the large fragment, a mutation will occur, preferably a knock-out mutation. If the large insert vector library is large enough, it is likely that the resulting library after exposure to transposase and transposable elements will contain mutation of essentially every gene of the target organism.

Amplification of Disrupted Large Insert Vector

The disrupted large insert vectors or disrupted large DNA fragments produced by the present invention can optionally then be amplified. Amplification for large insert vectors other than large DNA fragments can be by growth in a suitable host after transforming the disrupted large insert vectors into a suitable host. Such a suitable host can be any cell or organism capable of transformation, but the preferred amplification host is a bacteria, more preferably *E. coli.* Preferably the host will be selected that is compatible with the replication and operational genes of the disrupted large insert vector. The host will also be one that will allow selection of transformants with the first selectable marker of the large insert vector. Methods of transformation are well known to those of skill in the art as well as techniques for selecting for transformed hosts and harvesting the amplified vectors. Other methods of amplification can also be used including PCR, especially when the large insert vector is a large DNA fragment.

Assessment of Randomness

The randomness (or completeness) of insertion of the transposable element into the large insert vectors of the large insert library can be assessed by preparing cosmid DNA and performing DNA sequencing directed from primers at either ends of the transposon. If insertions are well distributed, near complete sequencing of several hundred thousand insertions should cover the majority of the genome and many genes should have multiple tranposon insertions (alleles). In practice, transposon insertion randomness is assessed on one or a few cosmids and by restriction digests and sequencing.

Homologous Recombination in Host Organism

Disrupted large insert vectors, including large DNA fragments, can be inserted into a target host cell where homologous recombination is to take place. Methods of transformation of large insert vectors into a target host cell are known in the art. A preferred method of transformation particularly suited to filamentous fungi is electroporation or calcium mediated transformation of fungal protoplasts under suitable conditions. Suitable conditions include those described in, for example, Talbot et al. (1993) Plant Cell 5:1575–1590. The host organism can then be grown, and successfully transformed host cells can be selected using the second selectable marker and growing the host cells on an appropriate media. Verification of homologous recombination can be achieved using various methods known in the art. These include Southern blotting, PCR and restriction enzyme analysis.

A preferred target host cell is filamentous fungi, most preferably *Magnaporthe grisea,* the causative organism of rice blast disease. Blast disease poses a serious threat to the tropical rice growing regions of the world, which feed more than one third of the global population (Ou (1980) Plant Disease 64: 439–445). It is predicted that an additional 13 million tons of rice per year will be required to keep up with the rapid growth in rice-consuming populations (Lampe, (1994) Foreward, Rice Blast Disease, Manila, Philippines, CAB International, ix-x). However over 157 million tons of rice have been lost to rice blast disease from 1975 to 1990, a figure that equals 11 to 30% of global rice production (Baker et al., (1997) Science 276: 726–733).

The pathogen, *M. grisea,* a heterothallic Ascomycete, is also pathogenic to many forage grasses and economically important cereal crops including wheat, barley, and fingermillet. The rice blast fungus invades the above ground parts of the rice plant and in severe epidemics, large ellipsoid lesions can engulf the entire leaf surface. Sporulating lesions can spread the infection to the emerging seed panicle. This infection cycle is easily reproduced under controlled conditions allowing detailed studies of the disease process.

The method of the present invention can also be packaged as a kit containing the necessary components to perform the method of the invention as well as instructions for their use. Such a kit could comprise all or some of a transposable element, a matched transposase to the transposable element and a large insert vector to be used in constructing a large insert vector library. The could also include appropriate selectable markers either separate or incorporated into the large insert vector and the transposable element.

The methods, kits and components of the present invention are useful for producing mutations in a target organism by supplying to the target organism a piece of DNA that is well suited to facilitate the homolgous recombination of the piece of DNA and a similar piece of DNA in the host organism. In this way, mutations can be produced in a target organism in a systematic, high-throughput and site-directed manner to allow phenotypic mapping of many or essentially all the genes of an organism.

Following completion of the disruption of essentially all of the genes of a target organism, two collections are produced. The first is a collection of annotated insertion vectors. These can be placed in a database and searches used to locate vectors which can be used to mutate various genomic regions.

The second are collections of fungal strains that would have insertion events at various genomic locations. Fungal strains can be screened for desired phenotypes (e.g. loss of plant pathogenicity as described in Example 5), but can also be screened for changes in metabolites levels or gene expression. Depending on the fungal strain, phenotype screens can be used to look for losses of animal pathogenicity, changes in secreted metabolites (new low molecular weight metabolites resulting from pathway disruption) and changes in secreted protein levels (due to alterations in secretion pathways).

Sequencing of a large number of disrupted large insert vector events from either an individually selected large insert vector or from a genomic large insert vector library will yield multiple alleles or "hits' in the same gene. This allows it to be determined where in the gene the insertion occurs and what type of mutation is produced, e.g., knockout mutant, decreased biological activity of gene product, decreased level of expression of gene product. This allows a better prediction of the type of phenotype to be expected from mutation of the gene at a specified location along the gene DNA sequence. Such a situation is desirable for several reasons.

First, obtaining multiple alleles indicates that the knockout process is approaching saturation. This is analogous to the situation in a mutagenesis project where the recovery of multiple alleles indicates target saturation by a particular mutagen.

The second reason for this desired outcome is that multiple alleles would allow a diverse array of phenotypes to be recovered. For example, insertions near the amino terminal end of a gene would be expected to yield null (loss-of-function) phenotypes. However insertions in the promoter regions, carboxy-terminal region or the 3' untranslated leader region may yield different phenotypes. These phenotypes may include reduced activity of the gene product (as opposed to loss-of-function), or altered (increase, decrease or mis-timed) expression (in the case of promoter mutations). This array of possible phenotypes is a distinct advantage of the TAG-KO technology over the construction of strict "knock-out" or loss-of-function phenotypes. Multiple alleles would allow the more facile characterization of gene whose products play a rate limiting role in various processes.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Construction of Plasmids with a Transposon Containing a Selectable Marker

Figure 4:
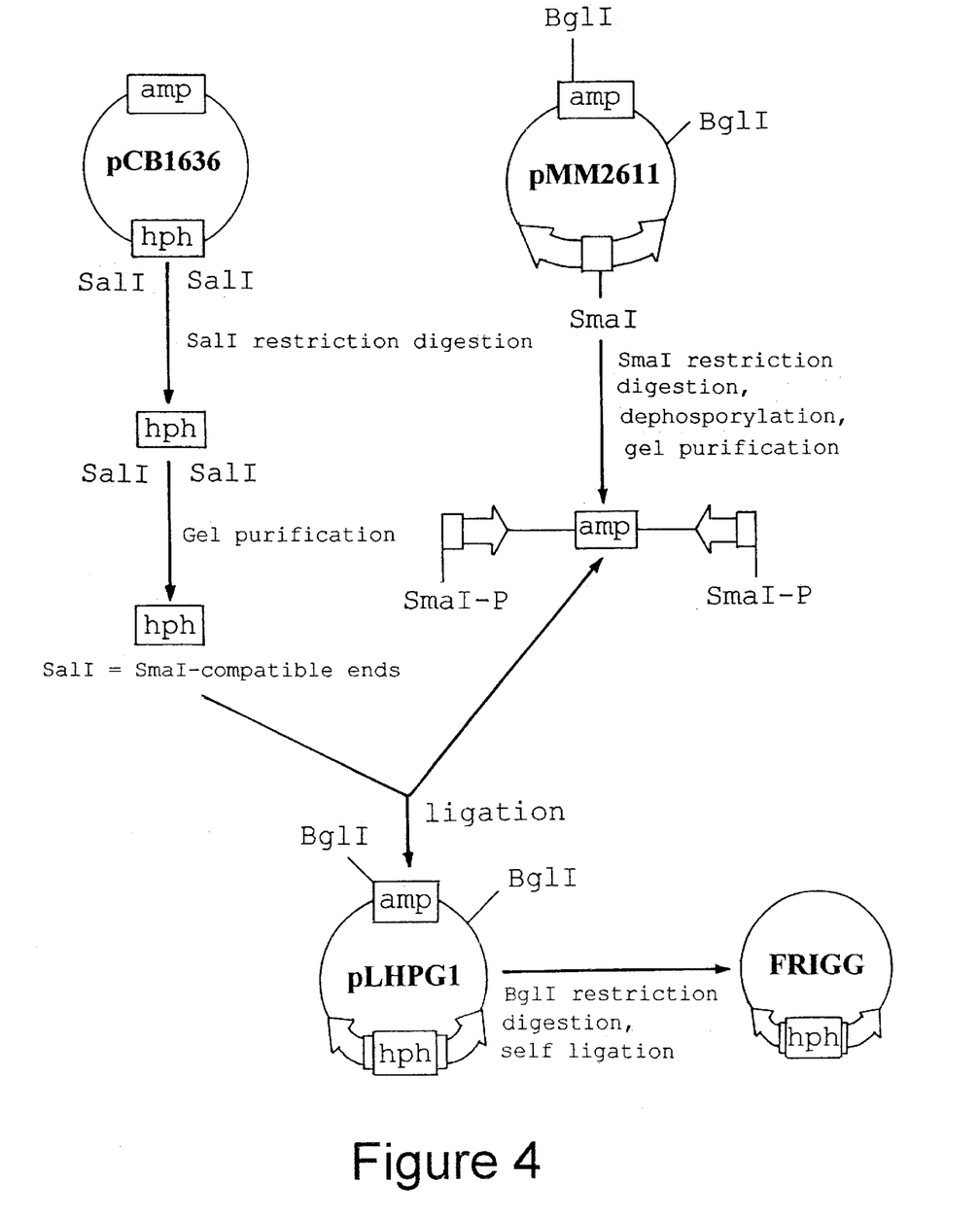
FIG. 4 shows the construction of a transposable element FRIGG as described in Example 1.

A. Construction of the FRIGG Transposon:

A sample transposon designated FRIGG, was constructed. pCB1636 contains a bacterial hygromycin B phosphotransferase (hph) gene (Gritz and Davies, (1983) Gene 25:179–188) under control of the *Aspergillus nidulans* trpC promoter and terminator (Mullaney et al, (1985) Mol Gen Genet 199:37–45). This plasmid was obtained from the Fungal Genetics Stock Center (Kansas City, Mont.). The following manipulations were done according to Sambrook et al. (1989) Molecular Cloning, a Laboratory Manual, Cold Spring Harbor Laboratory Press. A Sall fragment containing the trpC/hph gene from pCB1636 was end-repaired and ligated into the Smal cut, dephosphorylated transposon vector backbone pMM2611, (a derivative of pMM26 (Lampe et al., (1998) Genetics 149:179–187) to yield the plasmid PLHPG1. Competent *E. coli* XL1-BLUE cells (Stratagene) were transformed with pLHPG1 according to manufacturer's recommendation. Transformants were selected on LB agar (Sambrook et. al. (1989) *Molecular Cloning, A Laboratory Manual,* Cold Spring Harbor Laboratory Press.) containing 100 µg/ml ampicillin (Sigma Chem. Co.) and 35 µg/ml hygromycin B (Sigma Chem. Co.). DNA from individual transformants was prepared using a Wizard miniprep kit (Promega Co.) according to manufacturers suggestions. Restriction digestion of pLHPG1 with Bgll followed by self ligation caused the extinction of the ampicillin resistance gene, and yielded FRIGG, a transposon containing the Himar1 transposon and a hygromycin resistance gene. Transformation of *E. coli* cells was performed as described, and FRIGG-containing colonies selected for on LB agar containing 35 µg/ml hygromycin. FIG. 4 depicts the construction of FRIGG.

B. Construction of Other Transposons:

The method of Example 1A is followed except that in place of the pMM2611, the AT-2 (Perkin Elmer; Devine et al. (1997) Genome Res. 7:551–563), GPS-1 or GPS-2 transposable elements (New England Biolabs, Beverley, Mass.) were utilized.

Example 2

Construction of a Cosmid/BAC Library Containing Fungal Genes and a Selectable Marker Construction of cosmid and BAC libraries was performed as described in Sambrook et al. (1989) Molecular Cloning, a Laboratory Manual, Cold Spring Harbor Laboratory Press. An Amp resistant cosmid, coslf8 containing the adenylate cyclase (MAC1; Adachi and Hamer, (1998) The Plant Cell 10: 1361–1373) gene of *Magnaporthe grisea* was chosen to demonstrate the present invention. Alternatively, an insert in a bacterial artificial chromosome BAC 21D3 (Diaz-Perez et al. (1996) Fung. Genet. Biol. 20:280–288) was used as the large insert framework and chloramphenicol was used as the first selectable marker.

Example 3

Construction of Cosmids with Transposon Inserted into Fungal Genes

A. Transposition into a Cosmid:

Transposition on the cosmid framework was carried out as described by Lampe et al (1996) EMBO J. 15:5470–5479. In a total volume of 20 μl of transposition buffer (10% glycerol, 25 mM HEPES (pH 7.9 at room temperature (RT)), 250 μg of acetylated BSA, 2 mM DTT, 100 mM NaCI, 10 mM MgCI$_2$ or MnCI$_2$) the following components were combined: 1:1 molar amounts of donor:target (100 ng FRIGG: 1 μg pCosmacl), 0.2 μM Himar1 transposase (Lampe et al (1996) EMBO J. 15:5470–5479). The transposition mix was incubated 30 minutes at RT. The transposition reaction was stopped by addition of 80 μl of Stop solution (50 mM Tris-HCI, pH7.6, 0.5 mg/ml proteinase K, 10 mM EDTA, 250 μg/ml yeast tRNA to the tranposition reaction. The mixture was incubated one hour at 30° C. The DNA was precipitated by 50% v/v NH$_4$OAc, 200% v/v Ethanol 95% and resuspended on 10 μl TE buffer (Sambrook et al. (1989) Molecular Cloning, a Laboratory Manual, Cold Spring Harbor Laboratory Press.). 1 μl of the DNA solution was transformed into *E. coli* TOP10F' cells (InVitrogen) by electroporation according to manufacturer's recommendations. Cells were plated on L-medium containing 50 μg/ml ampicillin and 25 μg/ml hygromycin and incubated 2 days at 37° C. To verify DNA recovery after transposition and precipitation, an aliquot of the cells was plated on L-medium containing 100 μg/ml ampicillin and incubated at 37° C. overnight.

B. Transposition into a BAC:

Transposition on the BAC framework was carried out essentially as described by Lampe et al (1996) EMBO J. 15:5470–5479 except a BAC was used instead of a cosmid. In a total volume of 20 μl of transposition buffer (10% glycerol, 25 mM HEPES (pH7.9 at room temperature (RT)), 250 μg of acetylated BSA, 2 mM DTT, 100 mM NaCI, 10 mM MgCI$_2$ or MnCI$_2$) the following components were combined: 1:1 molar amounts of donor:target (100 ng from Example 1 of GPS-1, GPS-2 or AT-2:1 μg BAC from Example 2) and 0.2 μM GPS-1, GPS-2 or AT-2 transposase, respectively (Perkin Elmer, New England Biolabs). The transposition mix was incubated 30 minutes at RT. The transposition reaction was stopped by addition of 80 μl of Stop solution (50 mM Tris-HCI, pH7.6, 0.5 mg/ml proteinase K, 10 mM EDTA, 250 μg/ml yeast tRNA to the tranposition reaction. The mixture was incubated one hour at 30° C. The DNA was precipitated by 50% v/v NH$_4$OAc, 200% v/v Ethanol 95% and resuspended on 10 μl TE buffer (Sambrook et al. (1989) Molecular Cloning, a Laboratory Manual, Cold Spring Harbor Laboratory Press.). 1 μl of the DNA solution was transformed into *E. coli* TOP10F.' cells (InVitrogen) by electroporation according to manufacturer's recommendations. Cells were plated on L-medium containing 12.5 μg/ml chloramphenicol and 50 μg/ml hygromycin and incubated 2 days at 37° C. To verify DNA recovery after transposition and precipitation, an aliquot of the cells was plated on L-medium containing 100 μg/ml chloramphenicol and incubated at 37° C. overnight.

Example 4

High Throughput Preparation and Verification of Insertion of Transposon into Fungal Genes

*E. coli* strains containing cosmid pCosmac1 with transposon insertions were picked to 96 well growth blocks (Beckman Co.) containing 1.5 ml of TB (Terrific Broth, Sambrook et al. (1989) *Molecular Cloning, a Laboratory Manual,* Cold Spring Harbor Laboratory Press) supplemented with 100 ug/ml of ampicillin. Blocks were incubated with shaking at 37° C. overnight. *E. coli* cells were pellet by centrifugation and cosmids were isolated by a modified alkaline lysis method (Marra et. al. (1997) Genome Res. 7: 1072–1084). DNA quality was checked by electrophoresis on agarose gels. Cosmids were sequenced using a primer (TCGCTCTTGAAGGGAACTATG; SEQ ID NO:2) and commercial dideoxy sequencing kits (Big Dye Terminators, Perkin Elmer Co.). Sequencing reactions were analyzed on an AB1377 DNA sequencer.

DNA sequences adjacent to the site of the insertion were collected and used to search DNA and protein databases using the BLAST algorithms (Altshul et. al. (1997) Nucleic Acids Res. 25:3389–3402). A single insertion of FRIGG into the *M. grisea* adenylate cyclase gene at position nucleotide 3573 (Adachi and Hamer, (1998) The Plant Cell 10: 1361–1373) was chosen for further analysis. This cosmid was designated cpgformacFRIGG01a05.

The same procedure as above was performed on the BAC's except that chloramphenicol was used for selection instead of Amp, and appropriate primers were used. Multiple insertions were also observed in BAC's Example 5

Assembly of Transposon Alleles

Sequencing of a large number of disrupted large insert vector events from either an individually selected cosmid or from a genomic cosmid library will yield multiple alleles or "hits" in the same gene. This allows it to be determined where in the gene the insertion occurs and what type of mutation is produced, e.g., knock-out mutant, decreased biological activity of gene product, decreased level of expression of gene product. This allows a better prediction of the type of phenotype to be expected from mutation of the gene at a specified location along the gene DNA sequence.

Example 6

Preparation of Cosmid DNA in Bacteria for Transformation of the Fungus *Magnaporthe grisea*

Cosmid DNA was prepared by Qiagen midi-prep method (Qiagen Co.). Growth, storage and transformation of M. grisea strain Guy11was as previously described (Talbot et. al. (1993) The Plant Cell 5: 1575–1590). Approximately 10 ug of DNA was used in each transformation and contained 1×10$^6$ protoplasts. Cosmid DNA was linearized prior to transformation with PI-Pspl. Transformation was performed by the method of Talbot et. al. (1993) The Plant Cell 5: 1575–1590. Hygromycin resistant transformants were picked to oatmeal agar media (Crawford et. al. (1986) Genetics 114: 1111–1129). If argB or pyr-4 selectable markers are used, argB or pyr-4 resistant transformants are picked to oatmeal agar media.

Example 7

Verification of Homologous Integration of Transposon into Fungal Genes

In vivo disruption of the adenylate cyclase gene was verified at the molecular level by PCR analysis using primers GGCGTTGTGATCTGCAG; SEQ ID NO:3 and GGCCAGGAAACTCCCAG; SEQ ID NO:4 and by the phenotype showing the loss of growth integrity (sporulation) and appressorium formation (Adachi and Hamer, (1998) The Plant Cell 10: 1361–1373).

Example 8

Construction of pcosJH1

Removal of neomycin resistance gene and SV40 origin from pWE15. The cosmid vector pWE15 was obtained from Stratagene Corporation (La Jolla, Calif.). The sequence of pWE15 is available from Genbank, accession number X65279, and is described in Wahl et al. (1987) P.N.A.S. 84:2160–2164.

2 μg of pWE15 was digested with SalI (New England Biolabs) and SmaI (New England Biolabs) in 20 μl volume, with the manufacturer's recommended buffer. After successive phenol/CHCL₃ and CHCL₃ extraction, the plasmid DNA was ethanol-precipitated and resuspended in 15 ml of dH₂O. Added to the DNA solution was 2 μl of T4 DNA polymerase buffer (New England Biolabs) and 2 μl of 10 mM dNTPs. The mixture was heated for 5 min. at 70° C., then placed on ice. 1 μl of T4 DNA polymerase (New England Biolabs) was added, and the reaction mix incubated for 30 min. at 37° C., then 10 min at 75° C. to inactivate the T4 DNA polymerase.

A ligation mix consisting of 5 μl of SalI-SmaI digested pWE15, 3 ml dH2O, 1 μl of 10X T4 DNA ligase buffer (New England Biolabs) and 1 μl of T4 DNA ligase (New England Biolabs). Incubate overnight at 16° C. 20 μl of competent *E. coli* DH10B cells (GIBCO BRL) were electro-transformed with 1 μl ligation mix. Electroporation was performed with Gene Pulser II (BIO-RAD) and 0.1 mm cuvette, following the manufacturer's protocol. Transformants were selected on LB/ampicillin agar plates and subjected to restriction digestion analysis. The modified plasmid that resulted was designated as pWEX.

Introduction of XhoI site into pWEX. 2 μg of pWEX was digested with BamHI (New England Biolabs) in 20 μl volume. The blunting reaction was done as described above. One μl of shrimp alkaline phosphatase was added to the reaction mix, and incubated for 45 min. at 37° C., then 10 min at 70° C. to inactivate the alkaline phosphatase.

To ligate the XhoI linkers, a ligation mix was set up consisting of 2 μl dephosphorylated pWEX, 2 μl of XhoI linkers (10 OD/ml, New England Biolabs #1030), 4 μl dH₂O, 1 μl of 10X T4 DNA ligase buffer (New England Biolabs) and 1 μl of T4 DNA ligase, and incubated overnight at 16° C. The linker ligated DNA was purified by phenol/CHCL₃, and CHCL₃ extraction, and ethanol-precipitation. The purified DNA was resuspended in 20 μl of dH₂O.

Figure 1:
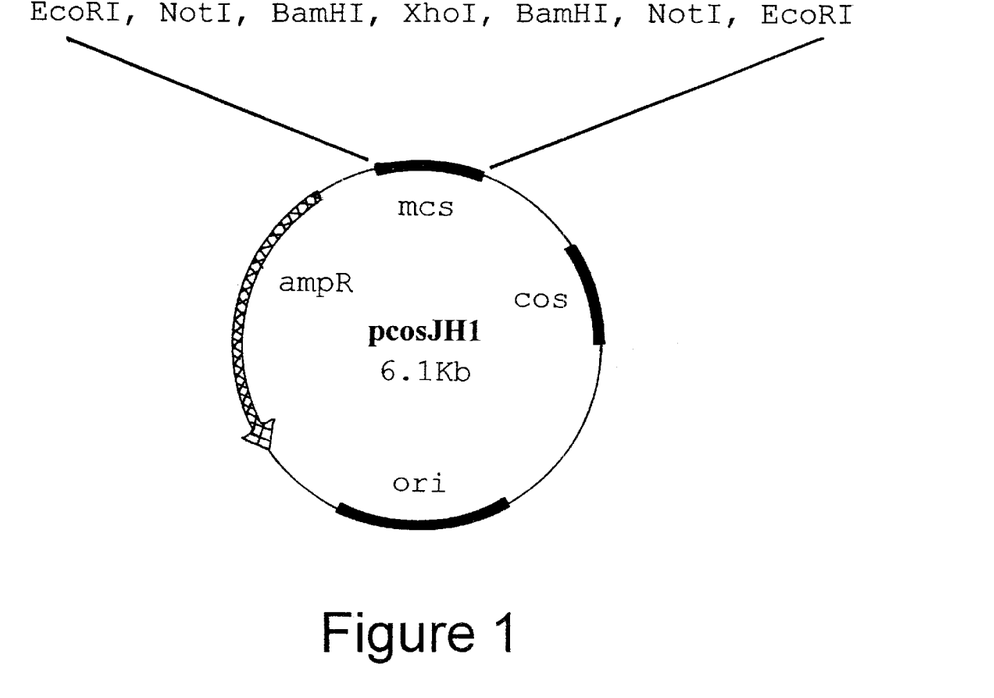
FIG. 1 is a schematic of the cosmid vector pcosJH1.

Linker digestion was performed with XhoI (New England Biolabs) in 50 μl dH₂O. The linker-ligated DNA was separated in 0.7% agarose gel and purified using QIAquick Gel Extraction Kit (QIAGEN) according to the manufacturer's protocol. Self-ligation, eletroporation and transformant selection were performed as described above. The resultant plasmid was designated pcosJH1. A map of the plasmid is shown in FIG. 1.

Example 9

Construction of pcosKA5 pcosKA5 is a cosmid vector suitable for genomic library construction and transposon mediated knockout transformation. It contains a bacterial origin of replication, ampicillin resistance gene, lambda cos packaging site derived from pWE15 (Stratagene) and modified multiple cloning site (MCS). The MCS includes an XhoI site for genomic DNA cloning and homing endonuclease sites (I-CeuI and PI-PspI) for generating long stretches of flanking DNA, which are favorable for homologous recombination.

Vector construction.

Preparation of I-CeuI and PI-PspI adaptors. The homing endonuclease sites for I-CeuI and PI-PspI were introduced into pBluescript II KS+(Stratagene) SalI and ClaI sites, using synthesized linkers. The sequence of pBluescript II KS+is available at Genbank accession number X52327, and is described by Alting-Mees and Short (1989) Nucleic Acid Res. 17:9494.

The linkers had the following sequences:
(I-Ceu1) SEQ ID NO:5
  AGCGGCCCGTAACTATAACGGTCCTAAG-GTAGCGAAGGCCGCT
(I-Ceu2) SEQ ID NO:6
  AGCGGCCTTCGCTACCTTAGGACCGT-TATAGTTACGGGCCGCT
(PI-Psp1) SEQ ID NO:7
  AGCGGCCAAAATCCTGGCAAACAGCTAT-TATGGGTATTATGGGTGGCCG CT
(PI-Psp2) SEQ ID NO:8
  AGCGGCCACCCATAATACCCATAAT-AGCTGTTTGCCAGGATTTTGGCCG CT 5 μl of the synthesized linkers Ceu11 and Ceu12 (100 mM) were mixed together and denatured for 10 min at 95° C., then cooled to room temperature. 7 μl of dH2O, 2 μl 10X buffer (New England Biolabs) and 1 μl HaeIII(New England Biolabs) were added, then incubated overnight at 37° C. The HaeIII digest was extracted with phenol/CHCI3 and CHCI3, successively precipitated by ethanol, and resuspended in 20 μl dH2O. The PI-PspI adaptor was created with Pspl1 and Pspl2 by the same method.

Restriction digestion, blunting and dephosphorylation of pBluescript II. 2 μg of pBluescript II KS+ was digested with SalI (NEB) in 20 μl volume. The digest was extracted with phenol/CHCI3 and CHCI3, successively precipitated by ethanol, and resuspended in 15 μl dH2O. 2 μl of 10x T4 DNA polymerase buffer (NEB) and 2 μl of 10 mM dNTPs were added, the mixture heated 5 min at 70° C., then placed on ice. 1 μl of T4 DNA polymerase (NEB) was added, and the mixture incubated 30 min at 37° C., then 10 min at 75° C. to inactivate the polymerase. 1 μl of shrimp alkaline phosphatase (Stratagene) was added, then the mixture incubated for 45 min at 37° C., then 10 min at 70° C. to inactivate the shrimp alkaline phosphatase.

Ligation of the I-CeuI adaptor into pBluescript II KS+. The ligation mix consisted of 2 μl of dephosphorylated pBluescript II KS+, 2 μl of I-CeuI adaptor, 4 μl of dH2O, 1 μl 10X T4 DNA ligase buffer (NEB) and 1 μl T4 DNA ligase (NEB). Incubate overnight at 16° C.

Creating an MCS cassette. XhoI-EcoRV fragment from the resulting plasmid was reintroduced into the ApaI site of the same plasmid to create a MCS cassette of I-CeuI, PI-PspI, XhoI, CeuI, PI-PspI. 5 μg of I-CeuI/PI-PspI/pBS KS+ was double digested with EcoRV and XhoI(NEB) in 50 μl volume. The digest was extracted with phenol/CHCI3 and CHCI3, successively precipitated by ethanol, and resuspended in 15 μl dH2O.

T4 DNA polymerase was treated for blunting, as described above. After inactivation of T4 DNA polymerase, the 120 bp fragment containing the I-CeuI and PI-PspI sites was separated in 2% agarose gel and purified using QIAquick Gel Extraction Kit (QIAGEN) according to the manufacturer's protocol.

Restriction digestion, blunting and dephosphorylation. 2 μg of I-CeuI/PI-PspI/pBS KS+ was digested with ApaI (NEB) in 20 μl volume. Blunting and dephosphorylation was done as described above.

Ligation. The ligation mix consisted of 0.5 μl of dephosphorylated I-CeuI/PI-PspI/pBS KS+, 7.5 μl of I-CeuI/PI-PspI fragment, 1 μl of 10X T4 DNA ligase buffer (NEB) and 1 μl of T4 DNA ligase (NEB). Incubate overnight as 16° C.

Electroporation and transformant selection was performed as described in Example 1. Correct orientation of the modified MCS site was confirmed by DNA sequence analysis. The resulting plasmid was designated I-Ceul, PI-Pspl, Xhol, Ceul, PI-Pspl/pBS KS+.

Insertion into pcosJH1. The MCS cassette was excised with Kpnl and EcoRV and inserted into the BamHl site of the cosmid described in Example 1, pcosJH1.

5 µg of I-Ceul, PI-Pspl, Xhol, Ceul, PI-Pspl/pBS KS+ was double digested with EcoRV (NEB) and Kpnl (NEB) in 50 µl volume. The digest was extracted with phenol/CHCI$_3$ and CHCI$^3$, successively precipitated by ethanol, and resuspended in 15 µl dH2O. T4 DNA polymerase was treated for blunting, as described above. After inactivation of the T4 DNA polymerase, the modified MCS cassette (300 bp) was separated in 2% agarose gel and purified using QIAquick Gel Extraction Kit (QIAGEN) according to the manufacturer's protocol.

2 µg of pcosJH1 was digested with BamHI (NEB) in 20 µl volume. Blunting and dephosphorylation were performed as described above. The fragment was ligated into the vector as described above. Electroporation and transformant selection were as described above. The correct orientation of the modified MCS was confirmed by DNA sequence analysis. The resulting plasmid was named pcosKA5. A map of the plasmid is shown in FIG. 2, and the sequence is shown in SEQ ID NO:9.

Example 10

Construction of pPGFRKA1

PPGFRKA1 is a tight cosmid vector which is used for TAG-KO (transposon mediated knockout) and genomic cloning. The vector contains bacterial origin of replication from pMB1 (ATCC Number 37074; Ish-Horowicz et al. (1981) Nucl Acids Res 9:2989–2998), ampicillin resistance gene, lambda packaging cos site, and multiple cloning site. The multiple cloning site includes an Xhol site for genomic DNA cloning and homing endonuclease site (I-Ceul and PI-Pspl) for generating inserts with long flanking sequences that are favorable for homologous recombination.

The plasmid pMOB (Strathmann et al. (1991) Proc Natl Acad Sci 88:1247–1250.) was digested with Pstl and Sacl.

The minimal cos site was PCR amplified, and ligated into the digested plasmid. The oligomers as described in Example 2 were used to introduce an I-Ceul site into the Apal and Clal sites of PMOB; and a PI-Pspl site into Kpnl and HindIII sites of pMOB.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

What is claimed is:

1. A method for facilitating site directed homologous recombination in a filamentous fungus to produce mutants comprising:
   1) providing at least one cosmid, wherein said cosmid comprises genomic DNA from a target filamentous fungus and pcosKA5 vector comprising a first selectable marker functional for selection in bacteria;
   2) providing a second vector comprising a transposable element, said transposable element comprising a nucleotide sequence coding for a second selectable marker flanked on each side by an inverted repeat sequence, wherein said second selectable marker is bifunctional for selection in bacteria and in the target filamentous fungus, and wherein said inverted repeat sequences are functional as a binding site for a transposase;
   3) incubating at least one of said cosmids with said second vector in vitro, in the presence of a transposase specific for the inverted repeat sequences on said second vector, such that said transposable element transposes into said genomic DNA to produce a disrupted cosmid;
   4) amplifying said disrupted cosmid in a bacterial cell and selecting for the presence of said first and second selectable markers in said bacterial cell;
   5) introducing the disrupted cosmid amplified in step 4) into a target cell from said target filamentous fungus so that homologous recombination can occur between said genomic DNA in said disrupted cosmid and the genome of said target filamentous fungus and thereby produce a mutated target cell; and
   6) selecting for the presence of said second selectable marker and screening for successful homologous recombination produced by step 5) in said mutated target cell.

2. The method of claim of claim 1, wherein said genomic DNA comprises at least 30 kilobase pairs.

3. The method of claim 1, wherein said genomic DNA comprises at least 40 kilobase pairs.

4. The method of claim of claim 1, wherein said genomic DNA comprises at least 45 kilobase pairs.

* * * * *